United States Patent [19]
Hendriksen et al.

[11] Patent Number: 6,063,976
[45] Date of Patent: May 16, 2000

[54] PROCESS TO ALKYLATE AN AROMATIC WITH A DILUTE STREAM COMPRISING PROPYLENE AND ETHYLENE

[75] Inventors: Dan E. Hendriksen, Kingwood; James R. Lattner, Seabrook; Jos P. Wristers, Clear Lake Shores, all of Tex.

[73] Assignee: Exxon Chemical Patent Inc., Houston, Tex.

[21] Appl. No.: 09/135,919

[22] Filed: Aug. 18, 1998

Related U.S. Application Data

[60] Provisional application No. 60/055,999, Aug. 18, 1997.
[51] Int. Cl.$^7$ .............................. C07C 2/68; C07C 2/64; C07C 15/067
[52] U.S. Cl. .......................... 585/467; 585/448; 585/449
[58] Field of Search ................................ 585/448, 467, 585/449

[56] References Cited

U.S. PATENT DOCUMENTS

| | | | |
|---|---|---|---|
| Re. 28,341 | 2/1975 | Wadlinger et al. | 208/120 |
| 3,086,998 | 4/1963 | Hervert et al. | 260/671 |
| 3,308,069 | 3/1967 | Wadlinger et al. | 252/455 |
| 4,227,992 | 10/1980 | Garwood et al. | 208/46 |
| 4,387,259 | 6/1983 | Barile | 585/467 |
| 4,447,664 | 5/1984 | Murchison et al. | 585/323 |
| 4,508,837 | 4/1985 | Zones | 502/62 |
| 4,891,458 | 1/1990 | Innes et al. | 585/323 |
| 5,003,122 | 3/1991 | Fellmann et al. | 585/467 |
| 5,082,990 | 1/1992 | Hsieh et al. | 585/467 |
| 5,118,896 | 6/1992 | Steigelmann et al. | 585/467 |
| 5,149,894 | 9/1992 | Holtermann et al. | 585/467 |
| 5,395,513 | 3/1995 | Chin et al. | 208/135 |
| 5,453,554 | 9/1995 | Cheng et al. | 585/467 |
| 5,476,978 | 12/1995 | Smith, Jr. et al. | 585/323 |
| 5,602,290 | 2/1997 | Fallon | 585/448 |
| 5,756,872 | 5/1998 | Smith, Jr. et al. | 585/449 |

FOREIGN PATENT DOCUMENTS

| | | |
|---|---|---|
| 055046 | 6/1982 | European Pat. Off. . |
| 064328 | 11/1982 | European Pat. Off. . |
| 159846 | 10/1985 | European Pat. Off. . |
| 159847 | 10/1985 | European Pat. Off. . |
| 317907 | 5/1989 | European Pat. Off. . |
| 366515 | 12/1993 | European Pat. Off. . |
| 2024790 | 1/1980 | United Kingdom . |

*Primary Examiner*—Hien Tran
*Assistant Examiner*—Thuan D. Dang
*Attorney, Agent, or Firm*—James A. Zboray

[57] ABSTRACT

The present invention provides a method comprising (a) contacting a first reaction mixture comprising an aromatic and a dilute stream comprising ethylene and propylene with a large pore microporous solid acid catalyst, preferably a large pore zeolite catalyst, which is effective to promote alkylation of the aromatic under first conditions effective to maintain a liquid phase comprising the aromatic and effective to cause the propylene to alkylate said aromatic but substantially ineffective to cause the ethylene to alkylate said aromatic, forming propylated aromatic and a second dilute stream comprising ethylene but substantially depleted of propylene, and (b) recovering the propylated aromatic.

26 Claims, No Drawings

PROCESS TO ALKYLATE AN AROMATIC WITH A DILUTE STREAM COMPRISING PROPYLENE AND ETHYLENE

This application claims the benefit of U.S. Provisional Application Ser. No. 60/055,999, filed on Aug. 18, 1997.

FIELD OF THE INVENTION

The present invention relates to selective catalytic alkylation of aromatics, preferably benzene, using a dilute stream comprising ethylene and propylene.

BACKGROUND OF THE INVENTION

Alkylated aromatics serve as the foundation for producing a variety of useful petrochemicals. For instance, ethylbenzene, cumene, ethyltoluene, and isopropyl toluene (cymene), as well as other alkyl-substituted aromatics, are beneficial as feedstocks for the production of a variety of styrenic and phenolic polymer materials. Alkyl-substituted aromatics also are useful as high octane transportation fuels. The use of alkyl-substituted aromatics as blending agents for gasoline expands product volume and increases octane values. Aromatic alkylation processes also provide an economic method of reducing benzene content in gasoline.

Most current processes for producing alkylated aromatics require the use of substantially pure olefins as alkylating agents. More economical sources are needed for olefins, such as ethylene and propylene, which are relatively expensive to produce in substantially pure form.

Cheap sources of ethylene and propylene include refinery off-gases or tail gases, which contain dilute concentrations of both ethylene and propylene, and possibly higher olefins. An even more common source of a mixed ethylene/propylene feedstock is the effluent produced by the thermal cracking of hydrocarbon streams in olefin production operations. Such a cracking product generally is much higher in mixed olefin content than are refinery off-gases.

It would be economically desirable to use these refinery gas streams as alkylating agents to produce alkylated aromatics. Unfortunately, when a mixed olefin gas stream is used to alkylate aromatic compounds, a mixture of several types of alkylated aromatic products is produced. The mixed product typically includes both ethylbenzene and cumene, which are difficult to separate.

Economical methods are needed to use these dilute mixed olefin streams to selectively produce cumene in one stage and ethylbenzene in a second stage. Several U.S. patents suggest the use of a mixed ethylene/propylene stream to alkylate benzene, namely, U.S. Pat. No. 4,891,458 and U.S. Pat. No. 4,447,664. However, neither of these patents teaches or suggests a method in which cumene is selectively produced in a first stage and ethylbenzene is produced in a second stage.

U.S. Pat. No. 4,447,664 describes a method to alkylate aromatic hydrocarbons using as an alkylating agent a product stream from a Fischer-Tropsch reaction which contains dilute amounts of both ethylene and propylene. The patent teaches that the "selected alkylating agent" can be an "ethylene/propylene" mixture. The patent also teaches that, prior to the alkylation of the aromatic material, alkylating agents other than the selected alkylating agent must be substantially removed from the stream, preferably by distillation. A method besides distillation is given for removing propylene when propylene is not the selected alkylating agent. That method involves the conversion of propylene and higher olefins to fuel oil and gasoline, as described in U.S. Pat. No. 4,227,992. U.S. Pat. No. 4,447,664 does not teach a process in which propylene is selectively reacted out of the stream to produce cumene in a first stage and thereafter the remaining propylene-depleted stream comprising ethylene may be reacted with the aromatic in a second stage to produce ethylbenzene.

U.S. Pat. No. 4,891,458 also teaches that mixtures of olefins containing 2 to 4 carbon atoms can be used to alkylate the aromatic hydrocarbons. However, when referring more specifically to the production of cumene, the patent admits that only a small fraction of by-product ethylbenzene and n-propylbenzene can be economically removed by distillation. The patent concludes that the feedstock must contain very little ethylene and that a catalyst should be used which makes very little of these impurities.

U.S. Pat. No. 4,387,259 describes the use of an intermediate pore size zeolite—"ZSM-12"—to catalyze a reaction in which a mixed ethylene/propylene stream is reacted with a stream containing benzene to produce cumene but not ethylbenzene. A need exists to identify additional catalysts and catalyst systems for the selective production of cumene and, if desired, ethylbenzene, using readily available, low cost mixed ethylene/propylene streams as the alkylating agent.

SUMMARY OF THE INVENTION

The present invention provides a method to alkylate aromatics comprising (a) contacting a first reaction mixture comprising an aromatic and a dilute stream comprising ethylene and propylene of greater than 4 mole percent with a large pore microporous solid acid catalyst effective to promote alkylation of the aromatic under first conditions effective to maintain a liquid phase comprising the aromatic and effective to cause the propylene to alkylate the aromatic but substantially ineffective to cause the ethylene to alkylate said aromatic, forming propylated aromatic and a second dilute stream comprising ethylene but substantially depleted of propylene, and (b) recovering the propylated aromatic.

DETAILED DESCRIPTION OF THE INVENTION

The present invention provides a process for alkylating an aromatic which comprises contacting the stream comprising the aromatic, preferably benzene, with a dilute stream of olefins under at least partial liquid phase conditions in the presence of a suitable catalyst. In a preferred embodiment, a first dilute feed comprising both ethylene and propylene is used to alkylate a stream of benzene to form cumene. After removal of the cumene, the remaining $C_3^-$ minus stream can serve as a second feed comprising a dilute stream of ethylene, which is used to alkylate benzene to produce ethylbenzene. The ethylene and propylene need not be separated or concentrated before they are used as alkylating agents.

Dilute ethylene and propylene are found in various refinery gas streams, usually diluted with various unreactive gases, such as hydrogen, nitrogen, methane, ethane, propane, etc. Such gas streams include but are not necessarily limited to those produced by thermal cracking units, catalytic cracking units, thermal reforming units, coking units, polymerization units, etc. In the past, such refinery gas streams—known as "off-gases" or "tail gases"—have been burned for fuel because no economical process was available to use the olefins. The dilute olefins could only be used as alkylating agents if they were concentrated and/or separated, a procedure which was often too costly to produce mere alkylating agents. According to the present invention, the olefins can be used as alkylating agents without the need for expensive concentration and/or separation procedures.

In addition to containing olefins, such as ethylene, propylene, and various butenes, off-gases or tail gases contain varying quantities of nitrogen and hydrogen. A typical analysis of a useful refinery off-gas from a catalytic cracking unit is as follows, in mole percent: nitrogen, 4.0%; carbon monoxide, 0.2%; hydrogen, 5.4%; methane, 37.8%; ethylene, 10.3%; ethane, 24.7%; propylene, 6.4%; propane, 10.7%; and $C_4$ hydrocarbons, 0.5%. The total olefin content of this gas stream is 16.7%. Ammonia, $C_4$ and higher olefins, and (if feasible) hydrogen sulfide should be removed from the off-gas or tail gas before use as the alkylating stream of the present invention.

Suitable catalysts for use in the invention include, but are not necessarily limited to, large pore solid acid catalysts, preferably large pore microporous materials, such as zeolites and silicoaluminophosphates, and most preferably large pore zeolites. As used herein, the term "large pore" is defined to mean having about the same pore size as X faujasite zeolite, i.e., the pore windows of the structure are of about a size such as would be provided by 12-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

Preferred zeolites for use in the invention include, but are not necessarily limited to, LZY-84, Y zeolite, and zeolite beta, all of which are commercially available from UOP, Des Plaines, Ill. A most preferred zeolite is zeolite beta, which is commercially available from UOP, PQ Corporation, and Engelhard Corporation. Zeolite beta also may be manufactured, ammonium exchanged, and extruded as described in U.S. Pat. No. 4,891,458, incorporated herein by reference.

Zeolite beta is a synthetic crystalline aluminosilicate originally described in U.S. Pat. No. 3,308,069 and U.S. Pat. No. Re 28,341, incorporated herein by reference, as follows:

[XNa(1.0±0.1−X)TEA]AlO$_2$.Y SiO$_2$.W H$_2$O wherein X is less than 1, preferably less than 0.75, TEA represents tetraethylammonium ion, Y is greater than 5 and less than 100, and W is up to about 4, depending on the condition of dehydration and on the metal cation present. Sodium may be replaced by another metal ion using ion exchange techniques.

Zeolite beta catalysts also include materials prepared using templating agents other than tetraethylammonium hydroxide and materials having Si/Al atomic ratios greater than 100. Also, the zeolites described in European Patent Application Nos. 55,046 and 64,328 and British Patent Application No. 2,024,790, incorporated herein by reference, have structures and X-ray diffraction patterns very similar to that of zeolite beta and are included within the scope of the term "zeolite beta" as used herein.

The forms of zeolite beta which are most useful in the present invention are crystalline aluminosilicates having the empirical formula:

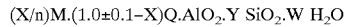

(X/n)M.(1.0±0.1−X)Q.AlO$_2$.Y SiO$_2$.W H$_2$O wherein X is less than 1, preferably less than 0.75, Y is greater than 5 and less than 100, W is up to about 4, M is a metal ion, n is the valence of M, and Q is a hydrogen ion, an ammonium ion, or an organic cation, or a mixture thereof. For purposes of the present invention, Y preferably is greater than 5 and less than about 50. Consequently, the silicon to aluminum atomic ratio in the above formula is greater than 5:1 and less than 100:1, and preferably greater than 5:1 and less than about 50:1. It also is contemplated that other elements, such as gallium, boron, and iron, can be variably substituted for aluminum in the above formula. Similarly, elements such as germanium and phosphorus can be substituted for silicon.

Suitable organic cations are those cations which are derived in aqueous solution from tetraethylammonium bromide or hydroxide, dibenzyl-1,4-diazabicyclo[2.2.2]octane chloride, dimethyldibenzyl ammonium chloride, 1,4-di (azoniumbicyclo[2.2.2]octane) butane dibromide or dihydroxide, and the like. These organic cations are known in the art and are described, for example, in European Patent Applications Nos. 159,846 and 159,847, and in U.S. Pat. No. 4,508,837, incorporated herein by reference. A preferred organic cation is tetraethylammonium ion.

M typically is a sodium ion from the original synthesis but also may be a metal ion added by ion exchange techniques. Suitable metal ions include those from Groups IA, IIA, or IIIA of the Periodic Table of the Elements, or a transition metal. Examples of such ions include ions of lithium, potassium, calcium, magnesium, barium, lanthanum, cerium, nickel, platinum, palladium, and the like.

For high catalytic activity, the zeolite beta preferably should be predominantly in its hydrogen ion form. Generally, the zeolite beta is converted to its hydrogen form by ammonium exchange followed by calcination. If the zeolite beta is synthesized with a high enough ratio of organonitrogen cation to sodium ion, calcination alone may be sufficient to activate the zeolite. After calcination, a major portion of the cation sites in the catalyst preferably should be occupied by hydrogen ions and/or rare earth ions. Most preferably, at least 80% of the cation sites in the catalyst are occupied by hydrogen ions and/or rare earth ions.

Pure zeolite may be used as a catalyst, but generally it is preferred to mix the zeolite powder with an inorganic oxide binder such as alumina, silica, silica/alumina, or naturally occurring clays and form the mixture into tablets or extrudates. The final tablets or extrudates may contain in the range of from about 1 to about 99 wt % catalyst. Usually, the zeolite beta content will range from about 10 to about 90 weight percent, and more typically from about 60 to about 80 weight percent. A preferred inorganic binder is alumina. The mixture may be formed into tablets or extrudates having the desired shape by methods well known in the art. The extrudates or tablets usually will be cylindrical in shape. Other shapes with enhanced surface-to-volume ratios, such as fluted or poly-lobed cylinders, can be employed to enhance mass transfer rates and, thus, catalytic activity.

Many aromatic hydrocarbons can be alkylated using the present invention. Preferred aromatic hydrocarbons are monocyclic aromatic hydrocarbons, i.e., benzene ring hydrocarbons. Suitable aromatic hydrocarbons include benzene, toluene, ortho-xylene, meta-xylene, para-xylene, ethyl-benzene, ortho-ethyltoluene, meta-ethyltoluene, para-ethyltoluene, 1,2,3-trimethylbenzene, 1,2,4-trimethylbenzene, 1,3,5-trimethylbenzene or mesitylene, normal propylbenzene, isopropylbenzene, etc. Higher molecular weight alkylaromatic hydrocarbons are also suitable and include aromatic hydrocarbons alkylated with olefin polymers. Such products frequently are referred to as alkylate, and include hexylbenzene, nonylbenzene, dodecyltoluene, pentadecyltoluene, etc. Very often, alkylate is obtained as a high boiling fraction in which the alkyl group attached to the aromatic nucleus varies in size from about $C_9$ to about $C_{18}$. Other suitable alkylatable aromatic hydrocarbons include those with two or more aryl groups, such as diphenyl, diphenylmethane, triphenyl, triphenylmethane, fluorene, stilbene, etc. Examples of other alkylatable aromatic hydrocarbons within the scope of the invention as starting materials comprise condensed benzene rings, and include, but are not necessarily limited to naphthalene, alpha-methylnaphthalene, beta-methylnaphthalene, anthracene, phenanthrene, naphthacene, rubrene, etc. The benzene ring hydrocarbons are preferred. Of the benzene ring hydrocarbons, benzene and toluene are preferred, and benzene is most preferred.

The stream may be pure aromatic, or a dilute stream. A preferred stream is pure benzene, another preferred stream is a dilute stream in which the only aromatic component is benzene. An example would be a benzene heartcut stream also comprising hexanes.

Various types of reactors can be used in the process. For example, the process may be carried out in batchwise fashion by adding the catalyst and aromatic feedstock to a stirred autoclave, heating to reaction temperature, and then slowly adding the olefinic feedstock. A heat transfer fluid can be circulated through the jacket of the autoclave, or a condenser can be provided, to remove the heat of reaction and maintain a constant temperature. Large scale industrial processes may employ a fixed bed reactor operating in an upflow or downflow mode or a moving bed reactor operating with concurrent or countercurrent catalyst and hydrocarbon flows. These reactors may contain a single catalyst bed or multiple beds, and may be equipped for the interstage addition of olefins and interstage cooling. Interstage olefin addition, and more nearly isothermal operation enhance product quality and catalyst life. A moving bed reactor makes possible the continuous removal of spent catalyst for regeneration and replacement by fresh or regenerated catalyst.

In order to selectively alkylate benzene to produce cumene, a suitable reactor preferably should be charged with a selected catalyst and a stream comprising at least a molar equivalent, preferably a stoichiometric excess of benzene (relative to the amount of propylene in the off-gas stream to be used). The reactor should be maintained at a temperature in the range of from about 80° C. to about 160° C., preferably at about 130° C. The off-gas or tail-gas stream comprising ethylene and propylene then should be introduced into the reactor, and the pressure should be adjusted to a level sufficient to maintain a liquid phase comprising primarily benzene and cumene. Pressures in the range of from about 350 kPa to about 7000 kPa should be sufficient, a preferred pressure being about 1590 kPa.

The "WHSV" or weight hourly space velocity, defined as weight feed per hour per weight of catalyst, should be sufficient to allow substantially all of the propylene, preferably all of the propylene, to react with the benzene; however, the residence time should be as short as possible to minimize reaction with ethylene and for economic reasons. The WHSV generally should be in the range of from about 0.5 $hr^{-1}$ to about 1,000 $hr^{-1}$, preferably in the range of from about 1 $hr^{-1}$ to about 20 $hr^{-1}$. The catalyst may contain other materials which act as inerts, fillers, or binders; therefore, the WHSV is calculated on the weight basis of aromatic plus olefin and zeolite.

The cumene may be separated from the remaining reaction mixture by distillation. The resulting stream should be "substantially depleted of propylene". As used herein, the phrase "substantially depleted of propylene" is defined to mean a propylene concentration of less than 4 mole percent. The benzene, catalyst, and gas comprising ethylene then should be heated to a temperature in the range of from about 170° C. to about 220° C., preferably to about 190° C., either in the same reactor or in a second reactor. The pressure should be adjusted to a level sufficient to maintain a liquid phase comprising primarily benzene. Pressures in the range of from about 1050 kPa to about 4200 kPa should be sufficient, a preferred range being from about 1400 to about 2800 kPa. Thereafter, the ethylbenzene should be collected by distillation. The catalyst may be regenerated, as needed, using known means.

Preferably, the reaction will be a continuous catalytic distillation similar to that described in U.S. Pat. No. 5,476,978, incorporated herein by reference. A continuous process requires the production of cumene in one reactor and the production of ethylbenzene in a separate reactor. In a continuous reaction, a second reactor should be charged with a selected catalyst and a stream comprising at least a molar equivalent, and preferably a stoichiometric excess of benzene (relative to the amount of ethylene in the gas from the first reactor). The gas exiting the first reactor should comprise ethylene, but should be substantially depleted of propylene. The gas from the first reactor should be charged to the second reactor. The mixture in the second reactor should be heated to a temperature in the range of from about 170° C. to about 220° C., preferably to about 190° C. The pressure in the second reactor should be adjusted to a level sufficient to maintain a liquid phase comprising primarily benzene. Pressures in the range of from about 1050 kPa to about 4200 kPa should be sufficient, a preferred pressure being about 2100 kPa.

The "WHSV" or weight hourly space velocity in the second reactor should be sufficient to allow substantially all of the ethylene to react with the benzene; however, the residence time should be as short as possible for economic reasons. The WHSV generally should be in the range of from about 0.5 $hr^{-1}$ to about 50 $hr^{-1}$, preferably in the range of from about 1 $hr^{-1}$ to about 20 $hr^{-1}$, on the weight basis of aromatic plus olefin and zeolite. Ethylbenzene produced in the second reactor should be collected by distillation. The catalyst may be regenerated periodically using known means.

The alkylation reactor effluents contain excess aromatic feed, monoalkylated product, polyalkylated products, and various impurities. The aromatic feed typically is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies. In most cases, the recovered monoalkylated product must be very pure. For example, current specifications call for about 99.9% cumene purity with less than 500 ppm each of ethylbenzene and butylbenzene.

Additional monoalkylated product may be produced by transalkylation. The polyalkylated products may be recycled to the alkylation reactor to undergo transalkylation or they may be reacted with additional aromatic feed in a separate reactor. Usually, it is preferred to blend the bottoms from the distillation of monoalkylated product with a stoichiometric excess of the aromatic feed, and react the mixture in a separate reactor over a suitable transalkylation catalyst. The transalkylation catalyst is preferably a catalyst comprising zeolite beta. The effluent from the transalkylation reactor is blended with alkylation reactor effluent and the combined stream distilled. A bleed may be taken from the polyalkylated product stream to remove unreactive heavies from the loop or the polyalkylated product stream may be distilled to remove heavies prior to transalkylation.

A series of experiments was conducted to produce cumene using different catalysts. The results are given in the following Table, and discussed in detail in the following examples. The following examples are provided to illustrate the invention, but are not to be construed as limiting the invention in any way except as indicated by the appended claims.

|  |  |  | Reaction | Liquid Product (weight %) | | | |
|---|---|---|---|---|---|---|---|
| Example No. | ° C. | Catalyst | Time (min) | Propylene- gm added | Cumene | Ethyl- benzene | Propylene Remaining |
| 1 | 130 | zeolite beta | 10 | 1.7 | 2.93 | 0.09 | 0.03 |
| 2 | 110 | zeolite beta | 10 | 1.8 | 1.44 | 0.04 | 0.02 |
| 3 | 90 | zeolite beta | 10 | 1.8 | 2.17 | 0.06 | 0 |
| 4 | 130 | zeolite beta | 30 | 1.9 | 6.46 | 0.46 | 0.04 |
| 5 | 150 | zeolite beta | 30 | 1.7 | 4.17 | 0.91 | 0.01 |
| 6 | 130 | LZY-84 | 30 | 1.8 | 2.61 | 0.14 | 0 |
| 7 | 90 | LZY-84 | 10 | 1.6 | 2.90 | 0.02 | 0.02 |
| 8 | 130 | SAPO-5 | 30 | 1.5 | 0.87 | 0.005 | 0.46 |
| 9 | 130 | zeolite beta | 30 | 1.2 | 3.82 | 0.46 | 0 |
| 10 | 130 | LZY-84 | 30 | 1.6 | 2.01 | 0.04 | 0.07 |

EXAMPLE 1

To a 300 cc stirred autoclave was charged benzene (100.1 g, anhydrous) and beta (1.00 g, ground UOP extrudate, dried at 200° C.). The autoclave was purged, pressurized with hydrogen to 100 kPa, and heated to 130° C. Ethylene was added sufficient to increase the total pressure by 100 kPa. Then propylene (1.7 g) was added to the autoclave, and additional hydrogen was added to bring the total pressure to 1590 kPa. After ten minutes with stirring, the autoclave was cooled rapidly to 6° C. and then slowly vented. The liquid contents were collected and analyzed. The cumene content was 2.93 wt % and the ethylbenzene content was 0.091 wt %. The unreacted propylene content was 0.03 weight %.

EXAMPLES 2–5

The procedure in Example I was repeated using zeolite beta as catalyst. The reaction time and temperature were varied, and the results are shown in the foregoing Table.

EXAMPLE 6

To a 300 cc stirred autoclave was charged benzene (102.0 g, anhydrous) and LZY-84 zeolite (1.00 g, ground UOP extrudate, dried at 200° C.). The autoclave was purged, pressurized with hydrogen to 100 kPa, and heated to 130° C. Ethylene was added sufficient to increase the total pressure by 100 kPa. Then propylene (1.8 g) was added to the autoclave, and additional hydrogen was added to bring the total pressure to 1467 kPa. After 30 minutes with stirring, the autoclave was cooled rapidly to 6° C. and then slowly vented. The liquid contents were collected and analyzed. The cumene content was 2.61 wt %, the ethylbenzene content was 0.14 wt %, and the unreacted propylene content was 0 wt %.

EXAMPLE 7

To a 300 cc stirred autoclave was charged benzene (102.9 g, anhydrous) and LZY-84 zeolite (1.09 g, ground UOP extrudate, dried at 200° C.). The autoclave was purged, pressurized with hydrogen to 100 kPa, and heated to 90° C. Ethylene was added sufficient to increase the total pressure by 100 kPa. Then propylene (1.6 g) was added to the autoclave, and additional hydrogen was added to bring the total pressure to 1460 kPa. After ten minutes with stirring, the autoclave was cooled rapidly to 6° C. and then slowly vented. The liquid contents were collected and analyzed. The cumene content was 2.90 wt %, the ethylbenzene content was 0.02 wt %, and the unreacted propylene content was 0.02 weight %.

Example 8 shows the use of SAPO-5 as a catalyst.

EXAMPLE 8

To a 300 cc stirred autoclave was charged benzene (102.0 g, anhydrous) and the silicoaluminophosphate catalyst known as SAPO-5 (1.05 g, ammonium ion-exchanged and calcined). The autoclave was purged, pressurized with hydrogen to 100 kPa, and heated to 130° C. Ethylene was added sufficient to increase the total pressure by 160 kPa. Then propylene (1.5 g) was added to the autoclave, and additional hydrogen was added to bring the total pressure to 1597 kPa. After 30 minutes with stirring, the autoclave was cooled rapidly to 6° C. and then slowly vented. The liquid contents were collected and analyzed. The cumene content was 0.87 wt %, the ethylbenzene content was 0.005 wt %. The unreacted propylene content was 0.46 weight %. Although the propylene conversion was substantially less than in the other examples, the ethylene conversion was low, as desired, and it is believed that the process could be modified to increase the propylene conversion.

Examples 9 and 10 show the use of dilute benzene with zeolite beta and LZY-84 as catalysts, respectively.

EXAMPLE 9

To a 300 cc stirred autoclave was charged benzene (10.7 g, anhydrous), hexanes (90.5 g, anhydrous), and zeolite beta (1.15 g, ground UOP extrudate, dried at 200° C.). The autoclave was purged, pressurized with hydrogen to 100 kPa, and heated to 130° C. Ethylene was added sufficient to increase the total pressure by 200 kPa. Then propylene (1.2 g) was added to the autoclave, and additional hydrogen was added to bring the total pressure to 1505 kPa. After thirty minutes with stirring, the autoclave was cooled rapidly to 6° C. and then slowly vented. The liquid contents were collected and analyzed. The cumene content was 3.82 wt % and the ethylbenzene content was 0.46 wt %. The unreacted propylene content was 0 weight %.

EXAMPLE 10

To a 300 cc stirred autoclave was charged benzene (10.1 g, anhydrous), hexanes (89.5 g, anhydrous), and LZY-84 zeolite (1.03 g, ground UOP extrudate, dried at 200° C.). The autoclave was purged, pressurized with hydrogen to 106 kPa, and heated to 130° C. Ethylene was added sufficient to increase the total pressure by 145 kPa. Then propylene (1.6 g) was added to the autoclave, and additional hydrogen was added to bring the total pressure to 1571 kPa. After thirty minutes with stirring, the autoclave was cooled rapidly to 5° C. and then slowly vented. The liquid contents were collected and analyzed. The cumene content was 2.01 wt % and the ethylbenzene content was 0.04 wt %. The unreacted propylene content was 0.07 weight %.

From the foregoing, it was concluded that cumene can be selectively formed using large pore zeolites when the reaction temperature is maintained at a level below that required to produce ethylbenzene and the pressure is maintained at a level sufficient to maintain a liquid phase comprising benzene. In several of the examples (4, 5, and 9), the resulting liquid content of ethylbenzene was relatively high. It was concluded that the reason for the higher levels of ethylbenzene was the longer reaction time (30 minutes), which apparently extended beyond the time necessary to react substantially all of the propylene with benzene to form cumene.

Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

We claim:

1. A method to alkylate aromatics comprising:
   contacting a first reaction mixture comprising an aromatic and a dilute stream comprising ethylene and propylene of greater than 4 mole percent with a large pore zeolite catalyst effective to promote alkylation of said aromatic under first conditions effective to maintain a liquid phase comprising said aromatic and effective to cause said propylene to alkylate said aromatic but substantially ineffective to cause said ethylene to alkylate said aromatic, forming propylated aromatic and a second dilute stream comprising ethylene but substantially depleted of propylene; and
   recovering said propylated aromatic.

2. The method of claim 1 further comprising:
   contacting said second dilute stream with a second catalyst under second conditions effective to maintain a liquid phase comprising said aromatic and effective to cause said ethylene to alkylate said aromatic, forming an ethylated aromatic.

3. The method of claim 2 further comprising recovering said ethylated aromatic.

4. A method to alkylate benzene comprising:
   contacting a first reaction mixture comprising benzene and a dilute stream comprising ethylene and propylene of greater than 4 mole percent with a large pore zeolite catalyst effective to promote alkylation of said benzene under first conditions effective to maintain a liquid phase comprising said benzene and effective to cause said propylene to alkylate said benzene but substantially ineffective to cause said ethylene to alkylate said benzene, forming cumene and a second dilute stream comprising ethylene but substantially depleted of propylene; and
   recovering said cumene.

5. The method of claim 4 further comprising:
   contacting said second dilute stream with a second catalyst under second conditions effective to maintain a liquid phase comprising said benzene and effective to cause said ethylene to alkylate said benzene, forming ethylbenzene.

6. The method of claim 5 further comprising recovering said ethylbenzene.

7. The method of claim 1 wherein said zeolite is selected from the group consisting of LZY-84, Y zeolites, and zeolite beta.

8. The method of claim 2 wherein said zeolite is selected from the group consisting of LZY-84, Y zeolites, and zeolite beta.

9. The method of claim 3 wherein said zeolite is selected from the group consisting of a LZY-84, Y zeolites, and zeolite beta.

10. The method of claim 4 wherein said zeolite is selected from the group consisting of LZY-84, Y zeolites, and zeolite beta.

11. The method of claim 5 wherein said zeolite is selected from the group consisting of a LZY-84, Y zeolites, and zeolite beta.

12. The method of claim 6 wherein said zeolite is selected from the group consisting of a LZY-84, Y zeolites, and zeolite beta.

13. The method of claim 1 wherein said first conditions comprise a temperature in the range of from about 80° C. to about 160° C.; and, a pressure in the range of from about 350 kPa to about 7000 kPa.

14. The method of claim 4 wherein said first conditions comprise a temperature in the range of from about 80° C. to about 160° C.; and, a pressure in the range of from about 350 kPa to about 7000 kPa.

15. The method of claim 7 wherein said first conditions comprise a temperature in the range of from about 80° C. to about 160° C.; and, a pressure in the range of from about 350 kPa to about 7000 kPa.

16. The method of claim 10 wherein said first conditions comprise a temperature in the range of from about 80° C. to about 160° C.; and, a pressure in the range of from about 350 kPa to about 7000 kPa.

17. A method comprising:
   contacting a first reaction mixture comprising benzene and a dilute stream comprising ethylene and propylene of greater than 4 mole percent with a zeolite beta catalyst under first conditions effective to maintain a liquid phase comprising said benzene and effective to cause said propylene to alkylate said benzene but substantially ineffective to cause said ethylene to alkylate said benzene, forming cumene and a second dilute stream comprising ethylene but substantially depleted of propylene; and
   recovering said cumene.

18. The method of claim 1 wherein said aromatic comprises a heartcut benzene stream comprising benzene and hexanes.

19. The method of claim 4 wherein said benzene comprises a heartcut benzene stream comprising benzene and hexanes.

20. The method of claim 17 wherein said benzene comprises a heartcut benzene stream comprising benzene and hexanes.

21. The method of claim 1 wherein said dilute stream comprising ethylene and propylene is selected from the group consisting of a refinery off-gas stream and an effluent produced by the thermal cracking of hydrocarbon streams in olefin production operations.

22. The method of claim 4 wherein said dilute stream comprising ethylene and propylene is selected from the group consisting of a refinery off-gas stream and an effluent produced by the thermal cracking of hydrocarbon streams in olefin production operations.

23. The method of claim 17 wherein said dilute stream comprising ethylene and propylene is selected from the group consisting of a refinery off-gas stream and an effluent produced by the thermal cracking of hydrocarbon streams in olefin production operations.

24. A method comprising:

contacting a first reaction mixture comprising an aromatic and a dilute stream comprising ethylene and propylene of greater than 4 mole percent with a large pore microporous solid acid catalyst effective to promote alkylation of said aromatic under first conditions effective to maintain a liquid phase comprising said aromatic and effective to cause said propylene to alkylate said aromatic but substantially ineffective to cause said ethylene to alkylate said aromatic, forming propylated aromatic and a second dilute stream comprising ethylene but substantially depleted of propylene; and recovering said propylated aromatic.

25. The method of claim 24 wherein said solid acid catalyst is selected from the group consisting of LZY-84, Y zeolites, zeolite beta, and SAPO-5.

26. The method of claim 25 wherein said solid acid catalyst is SAPO-5.

* * * * *